US 6,620,436 B1

(12) United States Patent
Rolf

(10) Patent No.: US 6,620,436 B1
(45) Date of Patent: Sep. 16, 2003

(54) MIXING AND DISPENSING PACKAGE FOR A WOUND DRESSING

(75) Inventor: David Rolf, Minneapolis, MN (US)

(73) Assignee: LecTec Corporation, Minnetonka, MN (US)

( * ) Notice: Subject to any disclaimer, the term of this patent is extended or adjusted under 35 U.S.C. 154(b) by 0 days.

(21) Appl. No.: 08/345,215

(22) Filed: Nov. 28, 1994

Related U.S. Application Data

(63) Continuation of application No. 07/913,151, filed on Jul. 14, 1992, now abandoned, which is a continuation-in-part of application No. 07/774,064, filed on Oct. 9, 1991.

(51) Int. Cl.$^7$ ................................................. A61F 13/00
(52) U.S. Cl. ........................ 424/489; 424/443; 424/445
(58) Field of Search ................................. 424/443, 445, 424/489; 426/108, 112, 113, 115

(56) References Cited

U.S. PATENT DOCUMENTS

| | | | | |
|---|---|---|---|---|
| 2,741,559 A | * | 4/1956 | Banowitz | 426/108 |
| 2,756,874 A | | 7/1956 | Erickson et al. | 206/47 |
| 3,008,835 A | * | 11/1961 | Madding | 426/108 |
| 3,207,420 A | | 9/1965 | Navarrete-Kindelán | 229/56 |
| 3,293,048 A | | 12/1966 | Kitterman | 99/171 |
| 3,637,132 A | | 1/1972 | Gray | 229/53 |
| 4,011,945 A | * | 3/1977 | Bourne et al. | 424/445 |
| 4,410,321 A | | 10/1983 | Pearson et al. | 604/56 |
| 4,550,825 A | | 11/1985 | Sutryn et al. | 206/222 |
| 4,596,713 A | | 6/1986 | Burdette | 426/107 |
| 4,770,295 A | | 9/1988 | Carveth et al. | 206/219 |
| 4,948,575 A | * | 8/1990 | Cole et al. | 424/445 |
| 5,089,606 A | | 2/1992 | Cole et al. | 536/54 |
| 5,770,229 A | * | 6/1998 | Tanihara et al. | 424/488 |
| 5,804,213 A | * | 9/1998 | Rolf | 424/445 |
| 5,844,013 A | * | 12/1998 | Kenndoff et al. | 521/137 |
| 5,853,749 A | * | 12/1998 | Hobbs | 424/443 |
| 6,406,712 B1 | * | 6/2002 | Rolf | 424/445 |

FOREIGN PATENT DOCUMENTS

| | | | | |
|---|---|---|---|---|
| EP | 0302536 | | 8/1989 | |
| GB | 2194144 A | | 3/1988 | |
| GB | 2229443 | * | 9/1990 | 424/445 |

* cited by examiner

Primary Examiner—Jose' G. Dees
(74) Attorney, Agent, or Firm—Schwegman, Lundberg, Woessner & Kluth, P.A.

(57) ABSTRACT

The invention provides a mixing and dispensing pouch for applying a wound dressing onto a wound. The pouch includes a pair of superimposed sheets, e.g., of plastic film, connected together at their edges. A pressure-rupturable seal is located between the super-imposed sheets and extends from one edge of the package to the other to form two compartments. The pressure-rupturable seal can be forced open manually by applying pressure on the exterior of the package with the hands so as to increase the hydrostatic pressure in a liquid, e.g., water contained in one compartment of the package causing the seal to rupture and the liquid to spurt through the ruptured seal, mixing with a dry wound dressing contained in the other compartment. If required, additional kneading of the package with the hands will mix the wound dressing for use as soon as it is expelled from the package. The package can be provided with notches to facilitate tearing the package open manually and, if desired, a pour spout with a frangible portion that can be removed so that the fluid dressing can be expelled through the spout.

21 Claims, 2 Drawing Sheets

MIXING AND DISPENSING PACKAGE FOR A WOUND DRESSING

This is a continuation of application Ser. No. 07/913,151, filed Jul. 14, 1992, which was abandoned upon the filing hereof and which is in turn a continuation-inpart of Ser. No. 07/774,064 filed Oct. 9, 1991.

FIELD OF THE INVENTION

This invention relates to a wound dressing package and more particularly to sterile packaging for a wound dressing that is to be mixed and dispensed from a single container.

BACKGROUND OF THE INVENTION

Numerous packages have been proposed for mixing and dispensing pharmaceutical products. For example, patent U.S. Pat. No. 5,089,606 describes a hydrogel foam which is mixed and dispensed from two parallel cylindrical syringes which force two separate liquid solutions through a mixing tube that contains a helical mixing blade for mixing the solutions together. The syringes and mixer are relatively expensive, complicated in construction and sub-ject to malfunction. In addition, they are wasteful because a certain amount of the product will remain in the mixer. By contrast, the present invention has as its general object the provision of an improved package and dispensing system in which syringes are not required and wherein a single container is used for storing, mixing and dispensing a pharmaceutical product.

U.S. Pat. No. 2,756,874 describes a compartmented bag and package for mixing two kinds of paste materials, e.g., dental paste, both of which are in fluid state. The paste formulations are placed in compartments that are separated by means of a removable clamp. The clamp, besides adding expense to the package because of the extra parts required, also adds extra assembly steps for forming the package and complicates mixing because one must become familiar with how to remove the clamp. By contrast, an object of the present invention is to reduce the cost of the package by eliminating the need for a clamp and yet reliably maintain constituents separate from one another.

The present invention has a variety of uses but is particularly beneficial for use with topical pharmaceutical products that are to be applied to the skin such as wound dressing that may, for example, contain water and a natural or synthetic hydrocolloid in particulate form. In order to provide outstanding shelf-life properties, it is an object to maintain liquid and solid pharmaceutical components separate from one another or to maintain at least some of the solid components separate from the water contained in the formulation.

The compositions described in U.S. Pat. No. 2,756,874 contain water in both compartments. This will usually reduce shelf life. In many products, and particularly pharmaceutical products, spoilage is of critical importance. Naturally, anything that tends to degrade the product prior to use could reduce its effectiveness which is usually unacceptable. To maintain aqueous and non-aqueous components separate from one another requires an effective barrier that will reliably prevent contact between them. Even a small leak can drastically reduce the shelf-life of the product. However, the more reliable the barrier that is provided, the more difficult it will be to remove the barrier to enable the components to be mixed. Accordingly, it is an important object to find a way of providing a package containing water or an aqueous solution, a separate dry pharmaceutical product, and a barrier between them that is reliable enough to prevent any mixing of the water with the dry constituents but which is still capable of being opened easily at ambient temperature using manual pressure.

Another form of multi-compartmented medicament container is described in U.S. Pat. No. 4,550,825. However, the construction is complicated by the need for a relatively expensive package having a cylinder and plunger of a special design. A major objective of the present invention is to provide reliable separation of liquid and solid components over extended periods with a provision for mixing them just before use while at the same time eliminating the need for moving mechanical parts.

These and other more detailed and specific objects of the invention will be apparent in view of the following specification which illustrates by way of example but a few of the various forms of the present invention that will be apparent to those skilled in the art within the scope of the appended claims.

SUMMARY OF THE INVENTION

The invention provides a mixing and dispensing pouch for a to be applied to the body of a patient. The mixing and dispensing pouch comprises a container body formed from flexible sheet material including a pair of superimposed sheets that are connected together at their edges. A transversely extending pressure-rupturable seal is located between the superimposed sheets and extends from one edge of the package to the other. The pressure-rupturable seal can be forced open manually solely by mechanical pressure applied from the exterior of the package at ambient temperature by pressing on the liquid-containing portion of the package with the hands to substantially increase the hydrostatic pressure in the liquid-containing portion, causing the liquid to spurt through the rupturable seal and mix with the dry constituents contained in the second compartment. If required, additional kneading of the package with the hands will mix the liquid and solid components to prepare the resulting composition for use as soon as it is expelled from the package. The package can contain weak areas, e.g., notches to facilitate tearing the package open manually and, if desired, can include a pour spout having a frangible portion that can be removed to open the spout for expelling the contents thereof through the spout by applying manual pressure to the walls of the package.

THE FIGURES

DETAILED DESCRIPTION OF THE INVENTION

Figure 1:
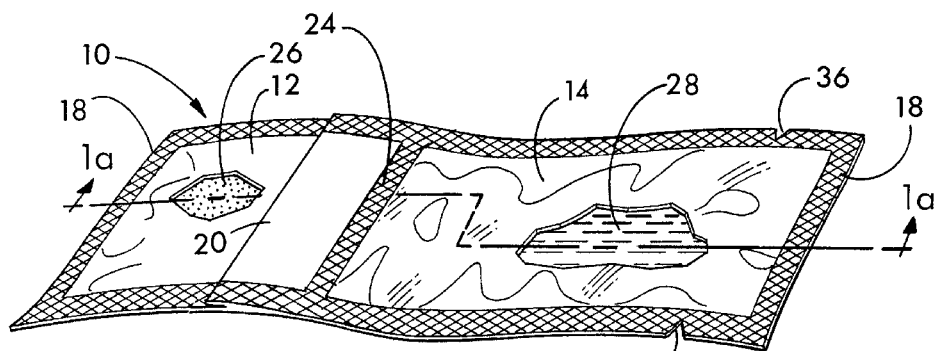
FIG. 1 is a perspective view illustrating one form of package used in accordance with the invention.

The invention is illustrated by way of example in FIGS. 1–7. Shown in FIGS. 1–7 is a container 10 or pouch formed from flexible sheet material including upper and lower superimposed sheets, in this case consisting of an upper sheet of a fibrous material, e.g., paper 12, an upper sheet of plastic film 14 and a lower sheet of plastic film 16. The sheets 12–16 are sealed together at their edges, e.g., by means of heat and pressure (a heat seal) to form a permanent peripheral fin seal 18 which extends around the entire container 10. The paper'sheet 12 is sealed to the plastic sheet 14 along a transverse heat seal line 20.

Extending between upper and lower edges of the pouch 10 is a rupturable seal 24 which includes a rupturable bond 22 (FIG. 7) between sheets 14 and 16. Communication inside the container 10 on either side of the rupturable seal 24 is prevented by means of bond 22. In this way, two separate compartments are formed to prevent contact between a dry particulate pharmaceutical constituent 26 on one side of seal 24 and liquid constituents 28 (water) on the other side. The term "water" herein includes aqueous solutions as well as pure water. The package 10 is shipped as shown in FIG. 1 with the water 28 separated by seal 24 from the dry particulate pharmaceutical constituents 26, thereby providing excellent shelf-life for the dry ingredients 26 which at this stage are inactive.

Figure 1A:
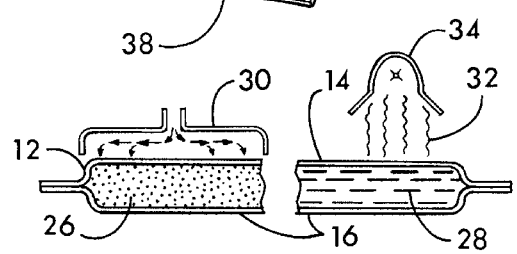
FIG. 1A is a semi-diagrammatic cross-sectional view taken on line 1A—1A of FIG. 1 showing sterilization of the package.

The package containing liquid and solid constituents 28, 26 is preferably sterilized. In this case, the contents are sterilized as shown in FIG. 1A. The paper sheet 12 is porous but impervious to pathogenic organisms. Its porosity-allows a sterilizing agent such as ethylene oxide gas to be introduced into the pouch 10 to the left of the barrier 24, e.g., through a gas applicator manifold 30. Exposure to ethylene oxide for a period of six hours has been found satisfactory. The liquid constituents 28 to the right of the barrier 24 are sterilized by being exposed to ionizing radiation 32 from a gamma radiation source 34 of $\geq 2.5$ Mrad.

The paper sheet 12 can be 37.5-pound per ream porous, waterproof paper formed from polytetrafluoroethylene, e.g., Tyvek® paper 1073B or 1059B (available from DuPont, Inc. of Wilmington, Del.), and the plastic sheets 14, 16 can be a 5 mil laminate, e.g. of polyethylene, aluminum foil, polyethylene and Mylar® as available from Technipaq Corporation of Chicago, Ill.

Another suitable plastic resinous film that can be used for the sheets 14 and 16 comprises a five-layer laminate which is formed from the following materials listed from the outside proceeding inwardly: first, a 0.5 mil layer 15a of saran-coated polyester film, e.g., M-30 which is a product code number of the DuPont Company; next, a polyacrylic adhesive layer 15b to bond the outer film layer to the third layer 15c which comprises a 0.6 mil layer of oriented biaxial nylon; next, an additional polyacrylic adhesive layer 15d; and finally, the innermost layer 15e which comprises a frangible substance that will separate under predetermined conditions. The bond 22 should be composed of a frangible material with a controlled, i.e., reduced peel strength. While various frangible heat-sealing substances can be used that are known to those skilled in the art, one preferred heat-sealing substance is an ionomer comprising a zinc salt of an ethylene acrylic acid copolymer known as Surlyn® by E.I. duPont of Wilmington, Del. The entire five-layer laminate 14, 16 is also available from the Hargro Flexible Packaging Company of Exton, Pa.

Thus, it can be seen that the rupturable seal 24 consists of a bond 22 wherein the frangible ionomer layer 15e on the inner surface of the sheets 14 and 16 is bonded to itself. An ionomer coating 15e has been found to be surprisingly effective in forming two kinds of bonds: first, the bond at 18 which is very difficult to break and the second at bond 22 which, although durable and strong, will still rupture reliably when manual pressure is applied to the liquid 28 to the right of the bond 22. Thus bond 22 can be reliably ruptured at ambient temperature solely by the application of external manual pressure applied to the liquid 28 in the compartment at the right in the figures.

The permanent seal 18 that extends around the entire periphery of the package 10 and the seal 24 between sheets 12 and 14 can be formed with a suitable heat sealer by applying heat and pressure; for example, at 430° F. for one second at a pressure of 60 to 80 psi.

The permanent seal 18 will typically have an average burst strength of about 4188 g/in at room temperature after one week of storage.

Figure 3:
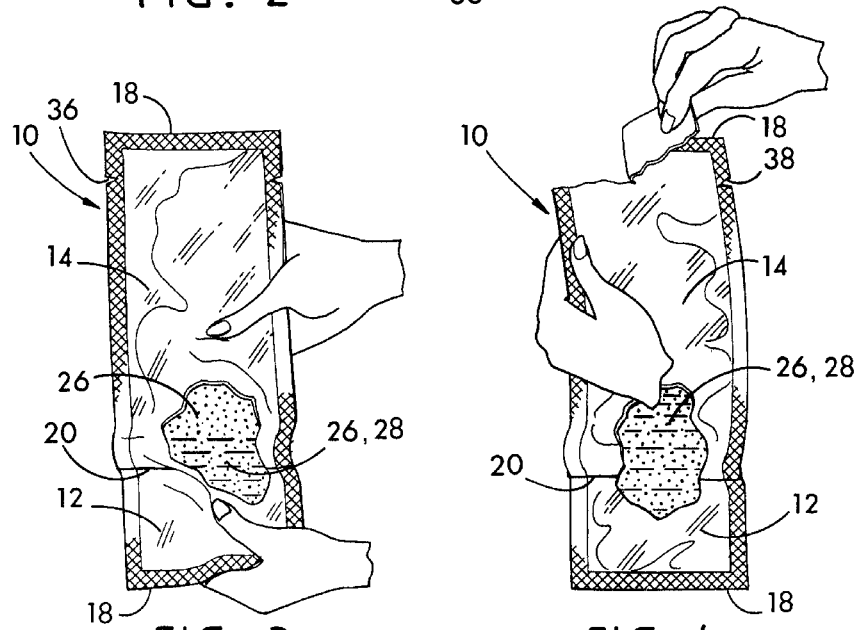
FIG. 3 is a view of the package of FIG. 1 on a smaller scale illustrating the mixing of its contents.

The rupturable seal 24 can be formed at a pressure of 60 psi applied for one-half second at 230° F. This will give the rupturable seal 24 a burst strength of about 450 grams/inch at room temperature after one week's storage. As a result, the seal 24 can be broken by applying manual pressure to the external walls of the fluid-containing compartment at the right of seal 24 at ambient temperature. This will cause the fluid to spurt through the bond 22 into the compartment at the left and become mixed with the dry constituents 26 to form a dispersion which can then immediately be expelled from the package and applied to the skin of a patient. After bond 22 is ruptured, mixing of solid and liquid ingredients can be accomplished manually, if needed, by kneading the pouch as shown in FIG. 3, for from a few seconds to about one minute until a homogeneous slurry is produced.

While performance will vary with different flexible sheet material, if the laminate referred to above is used the following performance will result. The fluid-containing compartment will have a moisture vapor transmission rate of about 0.024 grams/100 in$^2$/24 hr at 73° F. and 90% relative humidity. The oxygen permeability of the same compartment is 0.1982 cc/100 in$^2$/24 hr at 77° F. and 100% relative humidity.

Figure 2:
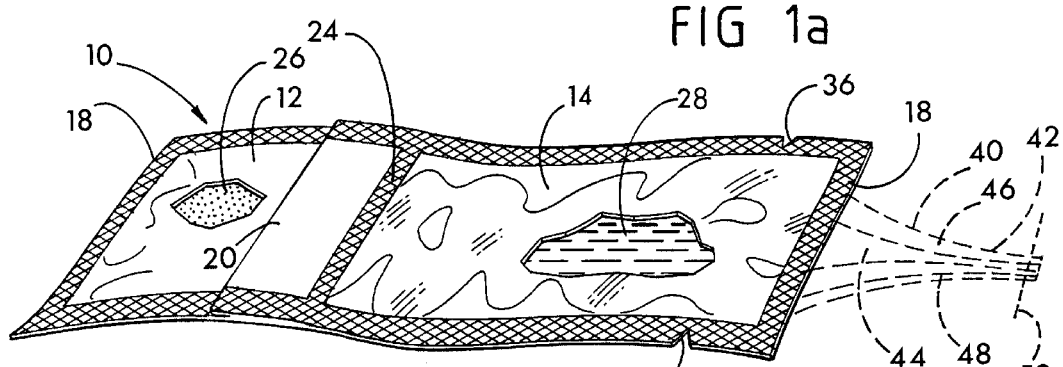
FIG. 2 is a view similar to FIG. 1 of an optional, modified form of the package with a dispensing spout.

Indentations 36, 38 can be provided at one end of the pouch to facilitate opening. In the alternative, as shown in FIG. 2, the pouch 10 can be provided with an extension 40 at one end which narrows to form a pointed dispensing spout 42 containing a central duct 44 between edge seals 46 and 48. The dispensing spout 42 can be cut with a scissors at 50 to provide an opening at the end of the spout through which the contents can be expelled when desired.

Figure 4:
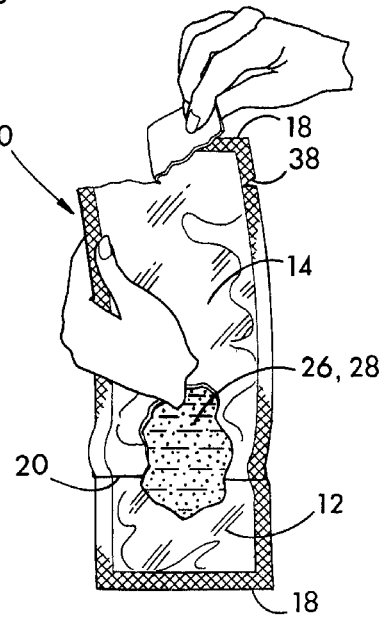
FIG. 4 is similar to FIG. 3 but shows the package being opened.
Figures 5, 6:
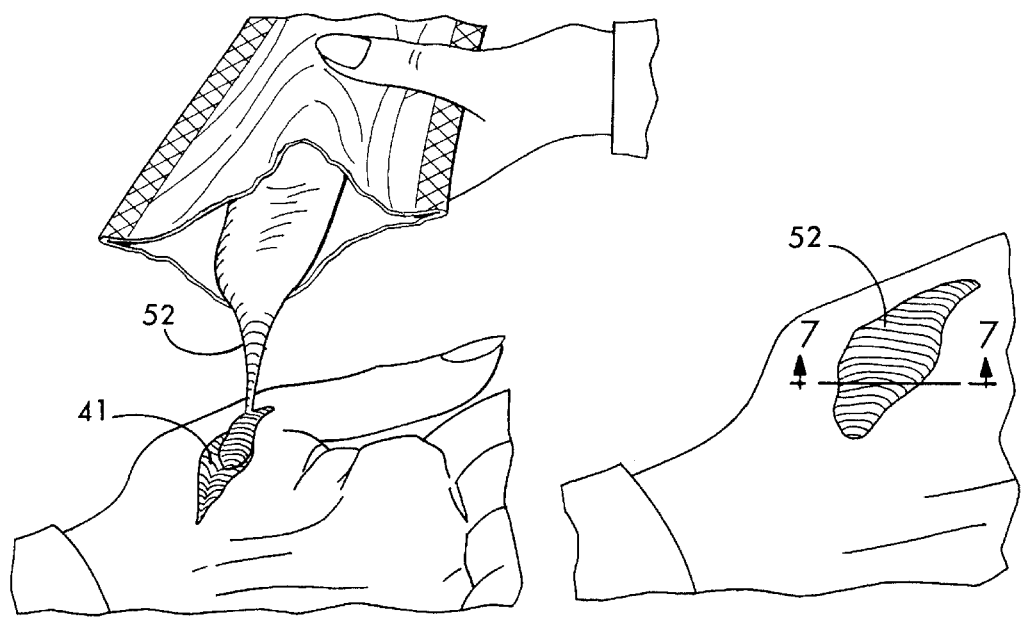
FIG. 5 illustrates the application of a pharmaceutical composition to the human body.
FIG. 6 illustrates the composition after being applied to a wound.
Figure 7:
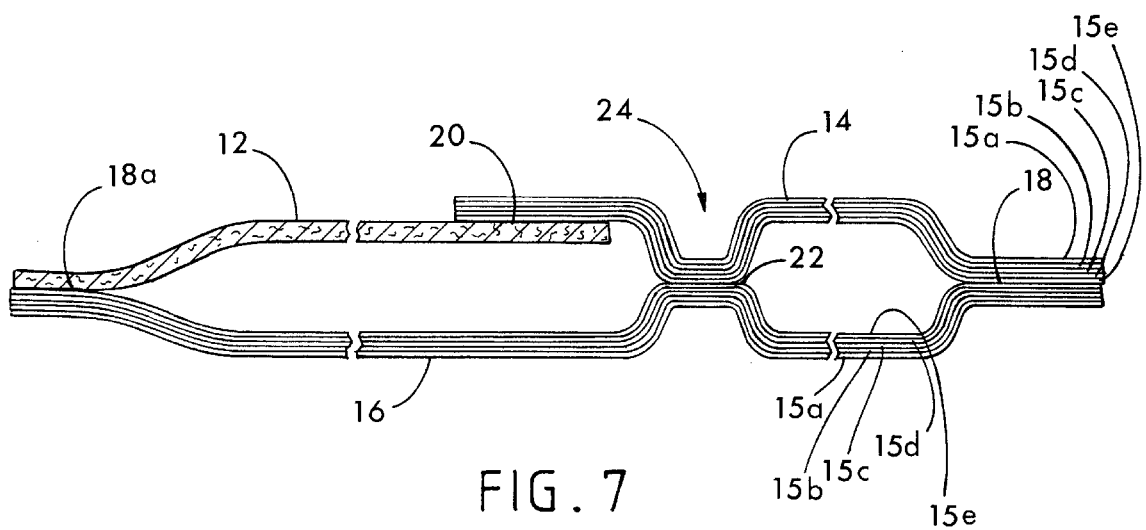
FIG. 7 is a greatly magnified diagrammatic vertical cross-sectional view taken on line 7—7 of FIG. 1.

As shown in FIG. 4, the end portion of the package 10 above the indentations 36, 38 can be removed to facilitate pouring material from the pouch. At this stage the aqueous hydrocolloid dispersion is a liquid and preferably sufficiently fluid to allow it to be applied as shown in FIG. 5. It will be noticed that the liquid hydrocolloid mixture 52, as it is poured from the package 10, e.g., onto a wound 41, will cover the wound.

The plastic film 14, 16 is substantially gas impervious while the porous sheet 12 is gas pervious. The combination of gas pervious and gas impervious materials in a single container has highly beneficial and unique properties, allowing water or an aqueous solution to be held on one side of the barrier 24 and a dry ingredient on the other side. However, both liquid and solid substances can be efficiently sterilized after packaging and while in the same package. In this way, the package 10 makes possible two kinds of sterilization in a single package. This is accomplished by providing two distinctly different components: a porous substance, e.g., paper 12 and plastic resinous film 14, 16.

This eliminates the need for filling the package under sterile conditions which can substantially complicate and increase the cost of assembling packages. Thus, the invention makes possible mixing two separate sterile components just before use. A sterile pharmaceutical product can thus be applied to the skin of a patient with no requirement for refrigeration.

The following method is used to form and use the package 10. A predetermined quantity of water 28 is sealed in the pouch 10 which is then sterilized, e.g., by gamma radiation applied to the liquid component 28 as described above. The pouch 10 is filled with the dry product 26. The pouch 10 containing the dry product 26 is then exposed to the sterilizing agency, in this case ethylene oxide gas as described above. The package 10 is then ready for use.

Many variations of the present invention within the scope of the appended claims will be apparent to those skilled in the art once the principles described above are understood.

What is claimed is:

1. A mixing and dispensing package for applying a wound dressing product to a patient, comprising:
   a flexible container-body formed from superimposed upper and lower flexible walls that form a flexible pouch having first and second edges on opposite sides of the package,
   said flexible walls comprising two different sheets located in two portions of the package for permitting the introduction of different sterilizing agencies into said portions of the package where said two different sheets are located,
   said sheets including
   (a) a first flexible sheet for allowing the introduction therethrough of a first sterilizing agency,
   (b) a second sheet for allowing the introduction therethrough of a second sterilizing agency, and
   (c) said second sheet has a different composition from said first sheet,
   a pressure-rupturable seal between the superimposed walls of said package, said seal extending from the first edge of the package to the second edge to divide said package into two separate compartments,
   a dry wound dressing in one compartment,
   water in the other compartment,
   said pressure-rupturable seal being able to be forced open by manual pressure applied to the exterior of the package by pressing on the water-containing compartment of the package with the hands to increase the hydrostatic pressure in the water-containing compartment and thereby force the water through the rupturable seal into the dry wound dressing contained in said one compartment to form a fluid dispersion for being dispensed from the package onto the wound,
   whereby said dry wound dressing is sterilized by a first sterilizing agency introduced into the package through the first sheet and the water sterilized by a second sterilizing agency introduced into the package the second sheet.

2. The mixing and dispensing package of claim 1 wherein said first sheet is a porous, gas permeable sheet for at least enclosing the dry wound dressing and said second sheet is a sheet of plastic film for enclosing the water within the package.

3. The package of claim 1 wherein one of the sheets is a gas permeable flexible sheet formed from fibers of an ethylene polymer.

4. The package of claim 1 wherein one of the sheets is a gas permeable sheet for at least enclosing the dry wound dressing and the gas permeable sheet allows the introduction therethrough of gas into the dry wound dressing for sterilizing the dressing.

5. The package of claim 1 wherein the package includes a pair of opposing walls of plastic film for enclosing and containing the water and the plastic film is permeable to ionizing radiation, whereby the water contained in the package can be sterilized by introducing the ionizing radiation into the water through the plastic film.

6. The package of claim 1 wherein at least some of the walls of the package comprise plastic film and the plastic film is bonded to itself by a seal produced by applying heat and pressure to the film to define said rupturable seal.

7. A mixing and dispensing package for applying a wound dressing product to a patient, comprising:
   a flexible container-body formed from superimposed upper and lower flexible walls that comprise a flexible pouch having first and second edges on opposite sides of the package,
   the upper and lower flexible walls of the package have an ionomer coating on an inside surface thereof,
   a rupturable seal in the package comprising a heat seal wherein the ionomer coating is bonded to itself to define a pressure-rupturable seal between the superimposed walls of said package with the ionomer coating, said seal extending from the first edge of the package to the second edge to divide said package into two separate compartments,
   a dry wound dressing in one compartment,
   water in the other compartment,
   said pressure-rupturable seal comprising being the ionomer able to be forced open by manual pressure applied to the exterior of the package by pressing on the water-containing compartment of the package with the hands to increase the hydrostatic pressure in the water-containing compartment and therefore the water through the rupturable seal into the dry wound dressing contained in the second compartment,
   a portion of the package being removable to provide an opening through which the dressing can be dispensed for being applied onto the wound,
   whereby the rupture of said heat seal wherein the ionomer is bonded to itself allows communication between the compartments and permits contacts between the contents of the separate compartments of said package.

8. The package of claim 7 wherein the ionomer coating is an ethylene acrylic acid copolymer to define said pressure-rupturable seal.

9. The package of claim 7 wherein the package includes a gas permeable flexible sheet as a wall of the package for allowing the introduction of a gas into the portion of the package containing the dry wound dressing for sterilizing the dry wound dressing.

10. The package of claim 9 wherein the gas permeable flexible sheet comprises a sheet formed from fibers of an ethylene polymer.

11. The package of claim 7 wherein the pressure-rupturable seal extends transversely across said package to divide the package into separate compartments, and the package includes a portion that can be cut or otherwise removed to provide a pour spout for expelling the contents of the package through the spout by exerting manual pressure on the walls of the package for applying the wound dressing to the body of a patient.

12. The package of claim 7 wherein opposing walls of the package comprise a plastic resinous film laminate including a first layer of saran-coated polyester film, a second polyacrylic adhesive layer, a third layer of nylon film, a fourth layer of polyacrylic adhesive, and a fifth layer comprising said ionomer coating.

13. The package of claim 12 wherein the ionomer coating is a salt of an ethylene acrylic acid copolymer.

14. A sterilizable mixing and dispensing package for a natural or synthetic hydratable solid in particulate form comprising,
- a flexible container body having first and second compartments,
- a rupturable barrier between the compartments for allowing communication therebetween when the barrier is eliminated to permit mixing of contents within the package,
- a natural or synthetic hydratable solid in particulate form in the first compartment,
- said first compartment having a wall formed from a porous polymeric sheet for allowing the entry of a gas into the first compartment through the pores in the sheet for sterilizing the particulate solid in said first compartment when the gas contacts the particulate solid therein,
- the second compartment has walls formed from a plastic resin that provides a watertight enclosure,
- water stored in said second compartment,
- said rupturable barrier being constructed and arranged to be opened by a person to allow the water in the second compartment to mix with the particulate solid in the first compartment for dispersing the particulate solid in the water to thereby form an aqueous dispersion within the package, and
- the porous polymeric sheet and plastic resin confine the aqueous dispersion within the package after mixing whereby the aqueous dispersion can be expelled from the package onto a surface through an outlet in the package other than the pores in the porous polymeric sheet.

15. The package of claim 14 wherein the rupturable barrier is a rupturable seal comprising an ionomer to provide a pressure-rupturable seal in the package.

16. The package of claim 15 wherein the ionomer coating is an ethylene acrylic acid copolymer to define said pressure-rupturable seal.

17. The package of claim 14 wherein the rupturable barrier is a heat seal formed between a first wall of said package and a second wall of said package.

18. The package of claim 4 wherein the gas permeable flexible sheet comprises a sheet formed from fibers of an ethylene polymer.

19. The sterilizable package of claim 14 wherein the hydratable solid is a hydrocolloid.

20. The sterilizable package of claim 14 wherein the package comprises a wall formed from a plastic film and a wall formed from said porous polymeric sheet with said barrier between said walls.

21. A sterilizable mixing and dispensing package for a wound dressing, comprising,
- a flexible pouch having a pair of compartments with a rupturable barrier between the compartments to allow mixing of material contained in the compartments after the barrier is ruptured,
- said compartments include a water-containing compartment formed from plastic film and,
- a hydrocolloid-containing compartment comprising a porous flexible sheet adapted to admit a sterilizing gas through pores in the flexible sheet for sterilizing the hydrocolloid contained therein, and
- after the barrier is ruptured the porous sheet and plastic film confine the hydrocolloid and water within the package, allowing a wound dressing formed from the mixture of the hydrocolloid and water to be expelled from the package onto a wound through an opening in the package.

* * * * *